(12) United States Patent
Fox et al.

(10) Patent No.: US 10,433,784 B2
(45) Date of Patent: Oct. 8, 2019

(54) SYSTEM AND METHOD FOR MAPPING THE LOCATIONS OF CAPTURED CONFOCAL IMAGES OF A LESION IN SKIN TISSUE

(71) Applicant: CALIBER IMAGING & DIAGNOSTICS, INC., Rochester, NY (US)

(72) Inventors: Christi Alessi Fox, Rochester, NY (US); Allison L. Reece, West Henrietta, NY (US); Allison L. Cramb, Rochester, NY (US); Aleksandar Sekulic, Scottsdale, AZ (US); David L. Swanson, Scottsdale, AZ (US)

(73) Assignee: Caliber Imaging & Diagnostics, Inc., Rochester, NY (US)

( * ) Notice: Subject to any disclaimer, the term of this patent is extended or adjusted under 35 U.S.C. 154(b) by 266 days.

(21) Appl. No.: 14/704,950

(22) Filed: May 5, 2015

(65) Prior Publication Data
US 2015/0313545 A1    Nov. 5, 2015

Related U.S. Application Data

(60) Provisional application No. 61/988,900, filed on May 5, 2014.

(51) Int. Cl.
*A61B 5/00* (2006.01)

(52) U.S. Cl.
CPC .......... *A61B 5/441* (2013.01); *A61B 5/0068* (2013.01); *A61B 5/444* (2013.01); *A61B 5/6841* (2013.01); *A61B 5/6833* (2013.01)

(58) Field of Classification Search
CPC .......................... A61B 5/0059; A61B 5/0084
See application file for complete search history.

(56) References Cited

U.S. PATENT DOCUMENTS

| 1,811,940 A | 6/1931 | Kappler |
|---|---|---|
| 5,020,088 A | 5/1991 | Tobin |
| (Continued) | | |

FOREIGN PATENT DOCUMENTS

| WO | WO/1996/021938 | 7/1996 |
|---|---|---|
| WO | WO/2000/049392 | 8/2000 |
| WO | WO 2014/032171 | 3/2014 |

OTHER PUBLICATIONS

Schmitt et al., "Optical characterization of dense tissues using low-coherence interferometry," Proc. of SPIE, vol. 1889, pp. 197-211, 1993.

(Continued)

*Primary Examiner* — Hien N Nguyen
(74) *Attorney, Agent, or Firm* — Kenneth J. LuKacher Law Group; Kenneth J. LuKacher (57) ABSTRACT

A system is provided having a guide member with features, such as grid and axes, which spatially correlate to tissue with a lesion adjacent the guide member, and a template device upon the tissue aligned with the features having a first aperture over the guide member, and a second aperture over the tissue with the lesion. A microscope captures one or more images of the tissue via the second aperture at one or more locations each spatially correlated with a location selected or being mapped along the guide member in the first aperture. Prior to imaging and template device placement, marks are recorded along the guide member when, as part of a tracing sheet, it is positioned in a folded state over the lesion. When returned to an unfolded state, the guide member once removed from the tracing guide sheet is positioned for use with the template device and microscope.

32 Claims, 9 Drawing Sheets

(56) References Cited

U.S. PATENT DOCUMENTS

| | | |
|---|---|---|
| 5,034,613 A | 7/1991 | Denk et al. |
| 5,103,338 A | 4/1992 | Crowley et al. |
| 5,156,150 A | 10/1992 | Lary |
| 5,383,234 A | 1/1995 | Russell |
| 5,383,472 A | 1/1995 | Devlin et al. |
| 5,428,690 A | 6/1995 | Bacus et al. |
| 5,532,874 A | 7/1996 | Stein |
| 5,574,594 A | 11/1996 | Fowler et al. |
| 5,701,175 A | 12/1997 | Kostizak et al. |
| 5,719,700 A | 2/1998 | Corcuff et al. |
| 5,788,639 A | 8/1998 | Zavislan et al. |
| 5,836,877 A | 11/1998 | Zavislan |
| 5,880,880 A | 3/1999 | Anderson et al. |
| 6,032,071 A | 2/2000 | Binder |
| 6,330,106 B1 | 12/2001 | Greenwald et al. |
| 6,411,434 B1 | 6/2002 | Eastman et al. |
| 6,860,855 B2 | 3/2005 | Shelby et al. |
| 7,194,118 B1 | 3/2007 | Harris et al. |
| 7,227,630 B1 | 6/2007 | Zavislan et al. |
| 7,394,592 B2 | 7/2008 | Fox et al. |
| 7,711,410 B2 | 5/2010 | Zavislan et al. |
| 7,864,996 B2 | 1/2011 | Hemmer et al. |
| 8,606,343 B2 | 12/2013 | Zavislan |
| 9,055,867 B2 | 6/2015 | Fox et al. |
| 2010/0234726 A1 | 9/2010 | Sirimanne et al. |
| 2013/0182318 A1* | 7/2013 | Eastman .............. B01L 3/508 359/398 |
| 2015/0223906 A1* | 8/2015 | O'Neill .............. A61B 6/0492 600/407 |

OTHER PUBLICATIONS

Rajadhyaksha et al., "Confocal laser microscope images tissue in vivo," Laser Focus World, pp. 119-127, Feb. 1997.

Rajadhyaksha et al., "In Vivo Confocal Scanning Laser Microscopy of Human Skin: Melanin Provides Strong Contrast," The Journal of Investigative Dermatology, vol. 104, No. 6, pp. 946-952, Jun. 1995.

Vivascope(R) 1500/3000, MAVIG GmbH, 2011.

Vivascope(R), Confocal Laser Scanning Microscopy—In Vivo Histology for Cellular Level Skin Analyses in Cosmetic Research and Dermopharmacy, MAVIG GmbH, pp. 1-20, 2011.

Canfield Scientific, Inc., Tracing Film, at least as early as May 4, 2014.

Karl Roessler et al., "Frameless Stereotactic Lesion Contour-guided Surgery Using a Computer-navigated Microscope", Surgical Neurology, vol. 49, pp. 282-289, 1998.

Davis et al., "The Electronic Pantograph: Amplifier Couples Microscope Stage to X-Y plotter", Brain Research Bulletin, vol. 15, pp. 533-536, 1985.

European Patent Application No. 15789823.0, Written Opinion, dated May 25, 2018.

* cited by examiner

SYSTEM AND METHOD FOR MAPPING THE LOCATIONS OF CAPTURED CONFOCAL IMAGES OF A LESION IN SKIN TISSUE

This application claims priority to U.S. Provisional Application No. 61/988,900, filed May 5, 2014, which is herein incorporated by reference.

FIELD OF THE INVENTION

The present invention relates to a system and method for mapping the locations of captured images of skin tissue, and in particular to a system having a microscope in which the locations of captured images of skin tissue, with respect to the surface thereof, spatially correspond to locations on a guide member affixed to the skin tissue beside the tissue being imaged. Such locations are selected or mapped using a coordinate system (such as a grid and/or axes) on the guide member spatially correlated with respect to a lesion in the skin tissue. The guide member may be part of a tracing guide sheet positionable between folded and unfolded states upon the tissue prior to imaging. In its folded state, such portion of the guide sheet providing the guide member is positioned over the lesion to establish such spatial correlation with the lesion and any surrounding skin tissue. Preferably, the microscope is a confocal microscope which captures confocal images.

BACKGROUND OF THE INVENTION

Confocal microscopes optically section tissue to produce microscopic images of tissue sections without requiring histological preparation of the tissue on slides (i.e., slicing, slide mounting, and staining). An example of a confocal microscope is the VivaScope® manufactured by Caliber Imaging & Diagnostics, Inc. "Caliber I.D." (formerly Lucid, Inc.) of Henrietta, N.Y. Other examples of confocal microscopes are described in U.S. Pat. Nos. 5,788,639, 5,880,880, and 7,394,592, and in articles by Milind Rajadhyaksha et al., "In vivo Confocal Scanning Laser Microscopy of Human Skin: Melanin provides strong contrast," The Journal of Investigative Dermatology, Volume 104, No. 6, June 1995, and Milind Rajadhyaksha and James M. Zavislan, "Confocal laser microscope images tissue in vivo," Laser Focus World, February 1997, pages 119-127. Further, optically sectioned microscopic images of tissue can be produced by optical coherence tomography or interferometry, such as described in Schmitt et al., "Optical characterization of disease tissues using low-coherence interferometry," Proc. of SPIE, Volume 1889 (1993), or by a two-photon laser microscope, such as described in U.S. Pat. No. 5,034,613. These confocal systems, although useful for microscopic examination of a tissue lesion or other abnormal tissue, have no capability for identifying locations on the surface of the tissue where the imaged lesion is within the tissue. Without such identification, the physician does not know after imaging the particular locations in the imaged tissue to carry out treatment of the lesion viewed in the images. Such treatment may include excising the tissue from the patient, radiation therapy, or ablation. Since treatment can harm healthy tissue which may lie near a lesion, precise location of the lesion is of importance. Also, without the capability to identify on the tissue surface the locations of an imaged lesion, it may be difficult for a physician to locate the lesion in future examinations for observing possible changes in the condition of the tissue when treatment of the lesion is deferred or is non-invasive.

SUMMARY OF THE INVENTION

Accordingly, it is an object of the present invention to provide an improved system and method for mapping the locations of captured confocal images of tissue with respect to the surface of the tissue.

It is a further object of the present invention to provide an improved system and method for mapping the locations of captured confocal images of skin tissue having a lesion using a guide member that spatially corresponds to locations along a grid and/or axes on a guide member affixed to the skin tissue adjacent the tissue being imaged.

Still another object of the present invention is to provide an improved system and method for mapping the locations of captured confocal images along a guide member spatially correlated to a lesion in tissue adjacent the guide member, in which such guide member after imaging is carried out and removed from the tissue may be relocated in the future adjacent the same lesion and spatially correlated thereto for re-imaging the lesion to assess for changes in such lesion.

Briefly described, the system has a guide member having a surface with features which spatially correlate to tissue with a lesion adjacent the guide member, and a template device upon the tissue aligned with such features having a first aperture located over the surface of the guide member, and a second aperture located over the tissue having at least the lesion disposed adjacent the guide member. A microscope in the system is operated to capture one or more images of the tissue via the second aperture at one or more locations in the tissue, in which each of the one or more locations spatially correlates with a location selected or being mapped along the guide member in the first aperture with respect to the lesion. One or more marks (e.g., lesion outline) may be present on the guide member which spatially correlate to the actual lesion in the tissue.

Preferably, the microscope is a confocal microscope which can optically form one or more microscopic sectional images under the surface of the tissue, but other microscopes which optically form microscopic sectional images may also be used which operate by two-photon microscopy or optical coherence tomography or interferometry (OCT).

To facilitate spatial alignment of the guide member and the template device, the features along the guide member may be provided in the form of at least an x-y grid. The template device has a first dimension extending longitudinally along the template device extending centrally through the first and second apertures and aligned parallel to the x axis of the grid of the guide member, and the first and second apertures each have a centrally oriented second dimension orthogonal to the first dimension aligned parallel to the y axis of grid of the guide member. Features, such as lines, grooves, or channels, are provided along the front of the template device extending along such first dimension and parallel second dimensions for use is aligning the guide member to the template device to provide the desired spatial correlation to the guide member.

With guide member temporarily coupled or affixed to the tissue, the template device is movable along the guide member to different locations spatially correlated to different locations in the tissue in images captured by the microscope. At each location, spatial correlation with respect to the guide member is maintained with the template device so that desired images are captured in the tissue at selected or mapped locations along the grid. Locations along the grid may be selected or mapped in an x, y Cartesian coordinate system along such x and y axes, in which a center (or fiducial mark) is provided on the guide member defining the center origin of the x and y axes in such coordinate system. Preferably, the grid has two diagonal axes through such center in addition to the x and y axes to define eight axes which may be numbered on the guide member for use in determining or recording locations where images were captured with respect to the grid. Also preferably the locations (or outline) of the lesion when recorded or marked on the guide member is at least approximately centered about such center of the grid.

A tracing guide sheet is used to establish the spatial correlation between the lesion, and the grid and axes on the guide member, to enable operation of the template device to guide imaging by the microscope along the guide member to selected or mapped locations. The tracing guide sheet has two portions with one portion providing the guide member. The portions fold over each other so that both portions extend along common orthogonal dimensions or axes in a folded state. A point or fiducial mark on the first portion (representing a center point of the grid) aligns with a point or fiducial mark on the second portion in the folded state. In the unfolded state, fiducial marks of the first and second portions of the tracing guide sheet dimensionally correspond to the distance between the center of the second and first apertures, respectively, of the template device along its longitudinal dimension. Prior to imaging and template device placement, marks are recorded along the guide member when, as part of a tracing guide sheet, it is positioned in a folded state over the lesion to establish spatial correlation of the features of the guide member to the lesion. When back in an unfolded state, the guide member upon removal from the tracing guide sheet is positioned for use with the template device and microscope.

Preferably, the tracing guide sheet has multiple transparent layers with the bottom layer being of adhesive material enabling temporary affixing of the tracing guide sheet onto tissue, a top layer of thin plastic film having first and second portions, and a middle layer also of such thin plastic film which adheres by static cling to the top layer to facilitate ease of peeling the top layer with the first portion for folding over the second portion of the tracing guide sheet. To enable folding over of the first portion upon at least partially the second portion of the tracing guide sheet in an accordion fold or tri-fold, an intermediate portion with two fold lines are provided between the first and second portions. Such fold lines represent perforations cut in the tracing guide sheet through the first, second, and bottom layers.

In order to use the tracing guide sheet prior to imaging and template device placement, the tracing guide sheet in first placed in its unfolded state upon the tissue and adheres thereto by its bottom adhesive layer, so that the lesion in the tissue is at least approximately centered with the fiducial mark of the second portion of the tracing guide sheet. Prior to placement onto the tissue, a punctum (dot centered within the lesion) is manually applied to the center of the lesion, and such punctum is then aligned with the fiducial mark of the second portion when the tracing guide sheet is applied to the tissue. One or more locations (or outline) of the lesion viewed through the second portion of the tracing guide sheet are then marked with a pen so as to acquire at least the margin of the lesion with respect to the surface of the tissue. The top layer of the first portion is then partially peeled from the second layer and folded in an accordion or tri-fold, using the intermediate portion between the two fold lines, over the top layer of the second portion to place the tracing guide sheet in its folded state. The top layer of the first portion may entirely cover, or partially cover the top layer of the second portion of the tracing guide sheet when folded there over. In the folded state, the fiducial marks along both the first and second portions align with each other. Such one or more locations (or outline) recorded on the second portion are then traced with a pen to provide such one or more locations (or outline) on the upper surface of the first portion which will provide the guide member. The first portion is then unfolded to place the tracing guide sheet back into its unfolded state. Next, all the layers of the tracing guide sheet providing the second portion and intermediate portion are removed from the tissue using the perforations providing the fold line between the intermediate portion and the first portion as a tear line, leaving the first portion to serve as the guide member as described above for use with the template device.

Optionally, rather than tracing onto the first portion, one or more locations (or outline) of the lesion viewed through the first and second portions (and the intermediate portion sandwiched there between) are manually recorded or marked on the upper surface of the first portion which will provide the guide member. This is less preferably since graphics such as grid lines and axes along the first portion may obscured view of the lesion.

The punctum of the lesion may be permanently marked on the tissue, such as with tattoo ink, so that the template device and second portion of a new guide sheet may be later realigned over the lesion for reimaging the lesion. Such new guide sheet may be the same as the tracing guide sheet described above, but without a grid, so that the guide member after removal from the tissue can be aligned along the new guide sheet for reimaging the same lesion at one or more times in the future, as desired. One or more photographs may be taken by a digital camera of the lesion and the first portion of the guide member prior to removal from the tissue for future realignment using a measuring device (e.g., ruler) to locate physical landmarks of the skin or body of the patient having the lesion.

A method is also provided for mapping the locations of captured images of a lesion in tissue having the steps of: providing a guide member having a surface with features which spatially correlate to tissue with a lesion adjacent the guide member; positioning a template device upon the tissue aligned with the features having a first aperture located over the surface of the guide member and a second aperture located over the tissue having at least the lesion; and capturing one or more images of the tissue via the second aperture at one or more locations in the tissue, in which each of the one or more locations spatially correlates with a location selected or being mapped along the guide member in the first aperture with respect to the lesion.

Preferably, the method further has the steps of: providing a coordinate system along the surface of the guide member aligned with the features to assist in selection or mapping the location along the guide member representing where each of the one or more locations in the tissue image(s) are captured by the microscope; affixing the guide member to the tissue; and moving the template device along the guide member to at least two different locations spatially correlated to at least two different locations in the tissue where the image(s) are captured by the microscope.

BRIEF DESCRIPTION OF THE DRAWINGS

The foregoing objects, features and advantages of the invention will become more apparent from a reading of the following description in connection with the accompanying drawings, in which:

FIGS. 12A and 12B are examples of a removed portion of the tracing guide sheet of FIG. 10 from the tissue with an outline of the lesion in the example shown in FIG. 10, in which FIG. 12B shows the top layer being peeled away;

DETAILED DESCRIPTION OF INVENTION

Figure 1:
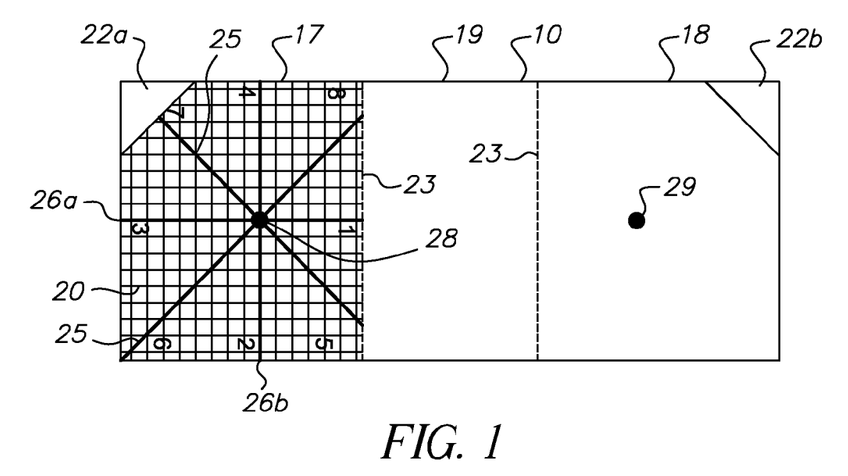
FIG. 1 is a top view of the tracing guide sheet used to provide the guide member in the system of the present invention for mapping locations of images captured by a microscope with respect to the surface of skin tissue having a lesion.

Referring to FIG. 1, a tracing guide sheet 10 of the system 11 (FIG. 15) is shown for providing a guide member 12 (FIG. 11) for mapping locations of microscopic sectional images with respect to the surface of tissue with a lesion captured by a confocal microscope 14 (FIG. 14) using a template device 16 (FIGS. 3A-3D).

Figure 2:
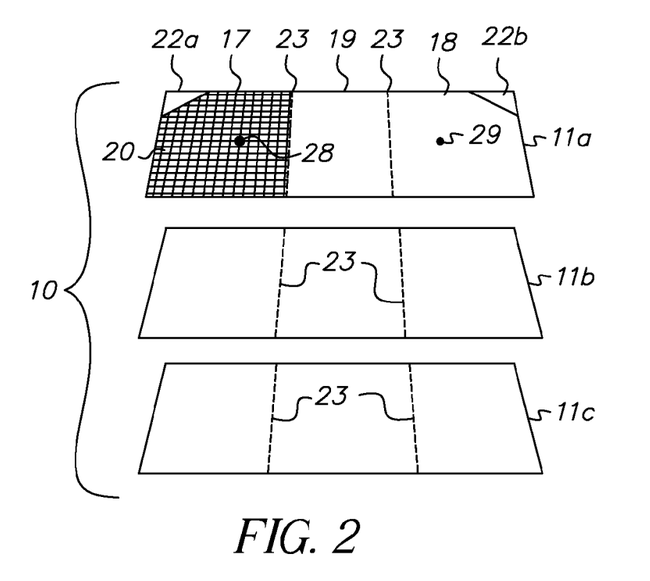
FIG. 2 is an exploded perspective view of the three layers of the tracing guide sheet of FIG. 1.

The guide sheet 10 has a first (grid) portion 17 with a set of x,y orthogonal grid lines 20, a second (clear) portion 18, and an intermediate portion 19 between first portion 17 and second portion 18. As shown in FIG. 2, guide sheet 10 is composed of three transparent layers having a top or upper layer 11a, and a middle layer 11b below the top layer 11a, and a bottom adhesive layer 11c. The adhesive layer 11c may be provided by double sided adhesive tape, adhesive backing material, or other medical grade adhesive, enabling temporary affixed placement of guide sheet 10 onto tissue. Layers 11a and 11b are of transparent medical grade plastic film or sheet, in which the top layer 11a adheres to the middle layer 11b by static cling. Tabs 22a and 22b are provided along two opposing corners of upper layer 11a to assist in locating the edge of the upper layer 11a when peeling or lifting up top layer 11a from middle layer 11b, as will be described below. Fold lines 23 are provided each between intermediate portion 19 and one of first and second portions 17 and 18. Such fold lines 23 extend through the layers 11a-c as shown in FIG. 2 and, in addition to enabling first portion 17 of the sheet to fold over the second portion 18, provide perforations through all layers 11a, 11b, and 11c to enable tear away of the portions 17-19 from each other as will be shown below.

The first portion 17 with x,y grid lines 20 preferably also has two diagonal lines 25 (or axes) which with an x axis 26a and a y axis 26b define eight axes, which may be numbered as shown in FIG. 1. As such diagonal lines and numbering are optional, they are not shown in FIGS. 2, 5-11, 13A and 13B. Fiducial marks (or dots) 28 and 29 are also provided along first portion 17 and second portion 18 of top sheet 11a of guide sheet 10. The grid lines 20, fiducial marks 28 and 29, tabs 22a and 22b, and if present diagonal lines 25 and numbers, represent graphics imprinted or printed on the surface of top layer 11a, such as by digital printing or lithographic press in one or more colors as desired. Preferably, grid lines 20 are printed in blue, and axes 25, 26a, 26b, and corner tabs 22a and 22b are printed in black. It had been found that such printing along tabs 22a and 22b reduce the static cling between layers 11a and 11b where tabs are present, thereby making peeling of layer 11a from layer 11b easier when needed using tabs 22a and 22b. As will be described later, axes 26a, 26b, grid 20, and axes 25 establish a coordinate system along the surface of first portion 17 providing guide member 12 to assist in selection or mapping of locations along guide member 12 representing where each location in tissue one or more images are captured by microscope 14.

Figure 3A:
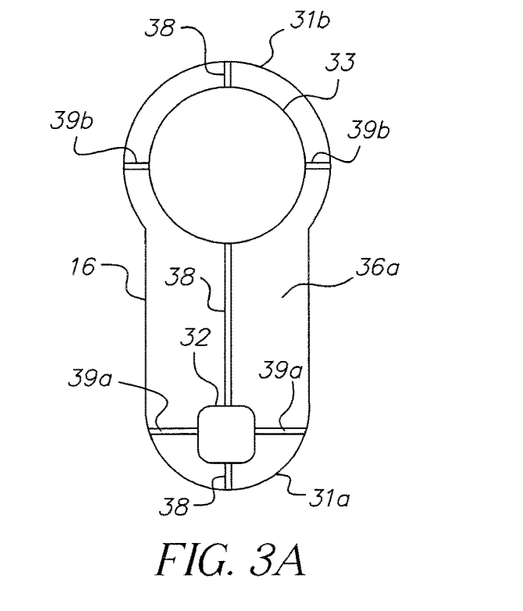
FIGS. 3A, 3B, and 3C are front, side, and front perspective views, respectively, of the template device of the system of the present invention.
Figure 3B:
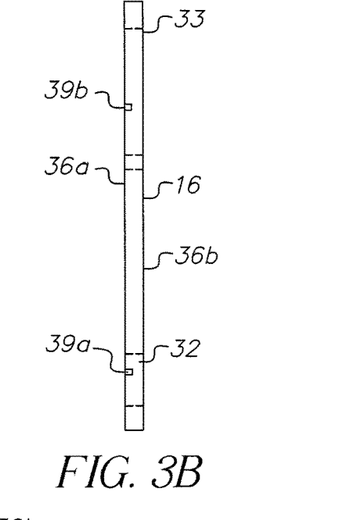
Figure 3C:
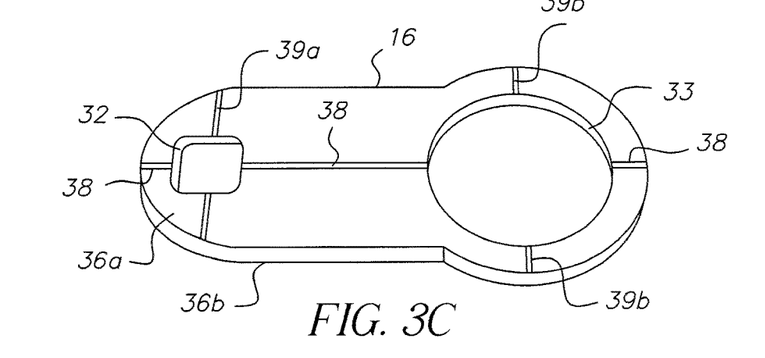
Figure 3D:
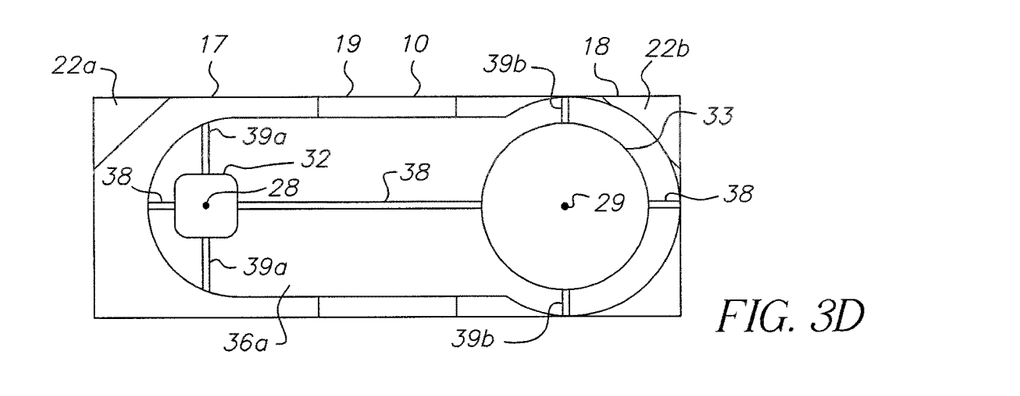
FIG. 3D is a schematic diagram illustrating the spatial relationship between the tracing guide sheet of FIG. 1 to the template device of FIGS. 3A-C where the two apertures of the template device are centered along two fiducial marks on the tracing guide sheet.
Figure 15:
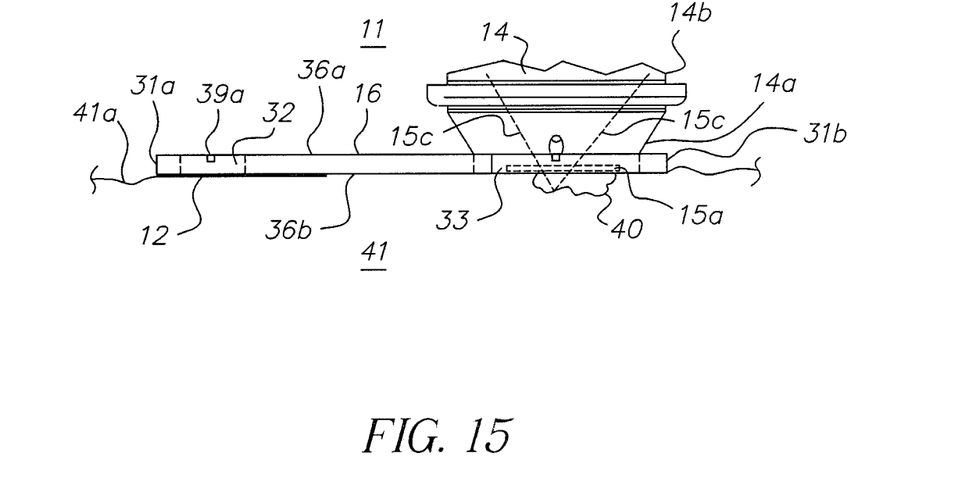
FIG. 15 shows a side view of the system of the present invention having the template device of FIGS. 3A, 3B, and 3C over the guide member of FIG. 11 aligned as shown for example in FIGS. 13A and 13B, and the microscope of FIG. 14 positioned with respect to the template device to view the lesion at locations mapped along the grid of the guide member, where the probe of the microscope is shown in broken view.

Referring to FIGS. 3A, 3B, and 3C, template device 16 has a body 30 with a first end 31a having a first aperture or opening 32, and a second end 31b with a second aperture or opening 33. The spatial relationship or orientation between guide sheet 10 to template device 16 is illustrated by showing template device 16 aligned over the guide sheet 10 in FIG. 3D, where apertures 32 and 33 of template device 16 are centered with respect to fiducial marks 28 and 29, respectively. Second aperture 33 is dimensioned to receive the front nose end 14a of a probe 14b of microscope 14 when placed against tissue viewable in such aperture, as shown in FIG. 15. The first aperture 32 is shown square, but may be other shape, so long as first aperture 32 is alignable over guide member 12 as will be described. Template device 16 may be made of rubber, such as EPDM, and having a durometer of 40 A, but other flexible material(s) may be used so that the template device's lower surface 36b may lie flush along tissue which may have a degree of curvature along the body of a person, including but not limited to skin tissue along the cheek and forehead, such as shown for example in FIG. 13C. First and second apertures 32 and 33 having a common longitudinal dimension or axis extending centrally through them, and parallel vertical dimensions or axes, orthogonal to such longitudinal dimension, centrally extending through each aperture 32 and 33. Lines, grooves, or channels 38 along the front surface 36a of template device 16 extend along such common longitudinal dimension or axis of template device 16, and lines, grooves, or channels 39a and 39b extend along the parallel vertical dimensions or axes of apertures 32 and 33, respectively.

For example, the tracing guide sheet 10 may have a length of 2.25 inches, width of 1 inch, and a total thickness of 0.0205 inches without a removable protective release liner. Layers 11a and 11b may each be 0.007 inches thick, and adhesive layer 11c may be 0.0065 inches thick. The length between fold lines 23 which define the intermediate portion 19 may be 0.322 inches, and the length between fiducial marks 28 and 29 may be 1.244 inches. Each box of grid 20 may be 1.5 mm square, but other dimensions may be used. The template device 16 may be 0.09 inches thick, and 2.0 inches in length, with the first aperture 32 being a square of 0.276 inches per side and slightly rounded corners. The end 31a of template device 16 may have an outer diameter of 1 inches, and second aperture 33 may be 0.75 inches in diameter. The centers of apertures 32 and 33 are 1.244 inches apart, but other dimensions may be used so long as the distance between the centers of the apertures 32 and 33 are equal to the distance between fiducial marks 28 and 29. Preferably, aperture 32 is smaller than aperture 33 along template device 16.

The process of providing guide member 12 on first portion 17 of guide sheet 10 is described below in connection with FIGS. 4-11 in the example of a lesion 40 which may be present in tissue 41. If the guide sheet 10 along top portion 17 has grid 20 and fiducial mark 28, but lacks numbered axes as shown in FIG. 1, such may be drawn with pen ink. Also, if diagonal axes 25 are not desired, only axes 26a and 26b need be drawn and numbered 1 through 4. Such axes are useful for designating direction of the lesion from the grid 20 center representing fiducial mark 28.

Figure 4:
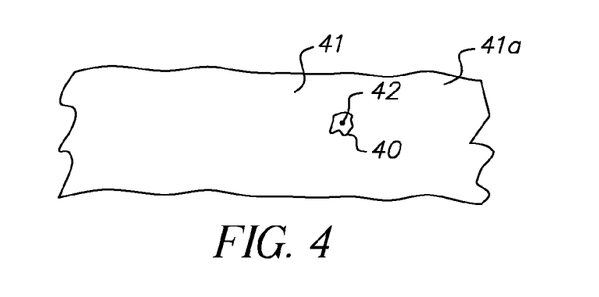
FIG. 4 is an illustration of an example of the skin tissue with a lesion in which the center of the lesion is shown marked with ink.
Figure 5:
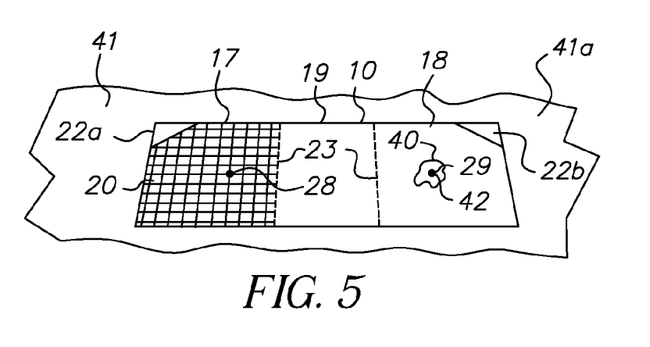
FIGS. 5-11 illustrate an example of use of the tracing guide sheet of FIG. 1 upon tissue with lesion of FIG. 4 to provide the guide member of the system of the present invention.
Figure 6:
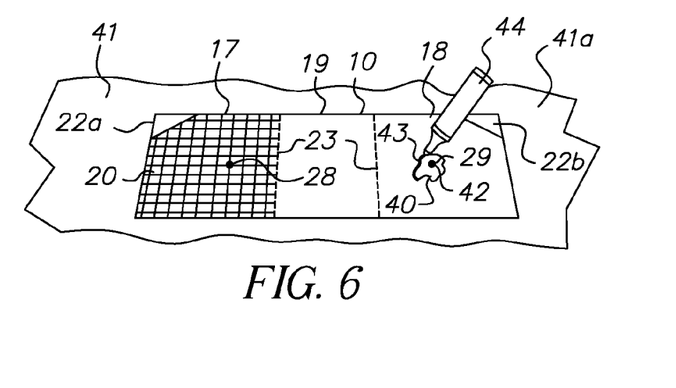
Figure 7:
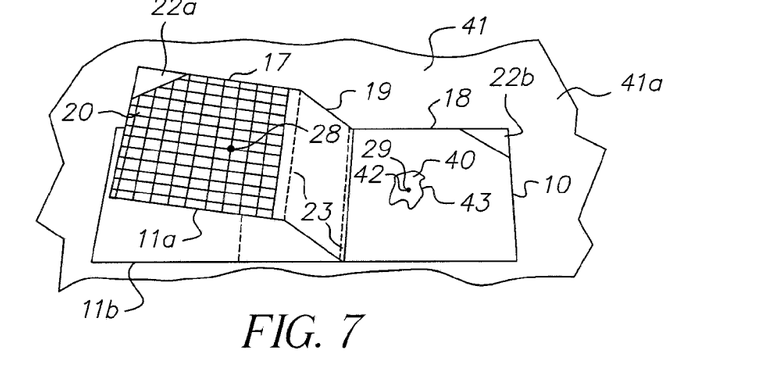

First, a dot (punctum) 42 of tattoo or other dark ink is manually applied to lesion 40 to mark the center of lesion 40 as defined by the user, as shown for example in FIG. 4. Next, if a protective release liner over the adhesive backing layer 11c is present along the back of guide sheet 10, such protected release liner is removed and discarded. Next, guide sheet 10 is applied onto the tissue surface 41a so that the dot 42 aligns with fiducial mark 29 on second portion 18 of the guide sheet (FIG. 5). The guide sheet 10 adheres to surface 41a of tissue 41 by adhesive layer 11c. An outline 43 of lesion 40 is then traced on second portion 18 using ink from a pen 44, such as a fine-tip permanent marking pen (FIG. 6). The traced outline may be along the boundary of lesion 40. Although described herein as an outline 43 of lesion 40, other marks may be made with pen 44 representative of areas or parts of the lesion of interest for examination, which may be in addition or alternative to outline 43. The guide sheet 10 is shown in its unfolded state in FIGS. 5 and 6.

Figure 8:
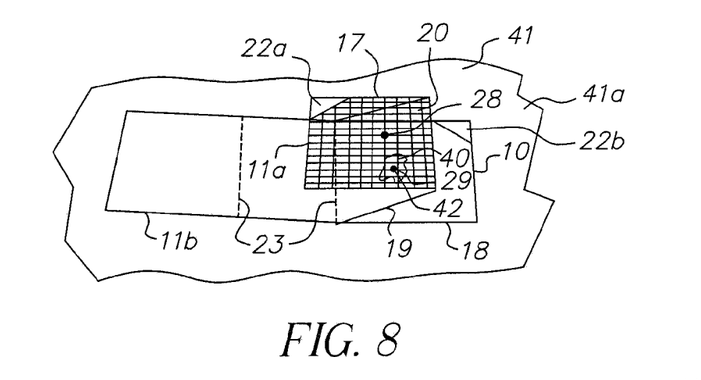
Figure 9:
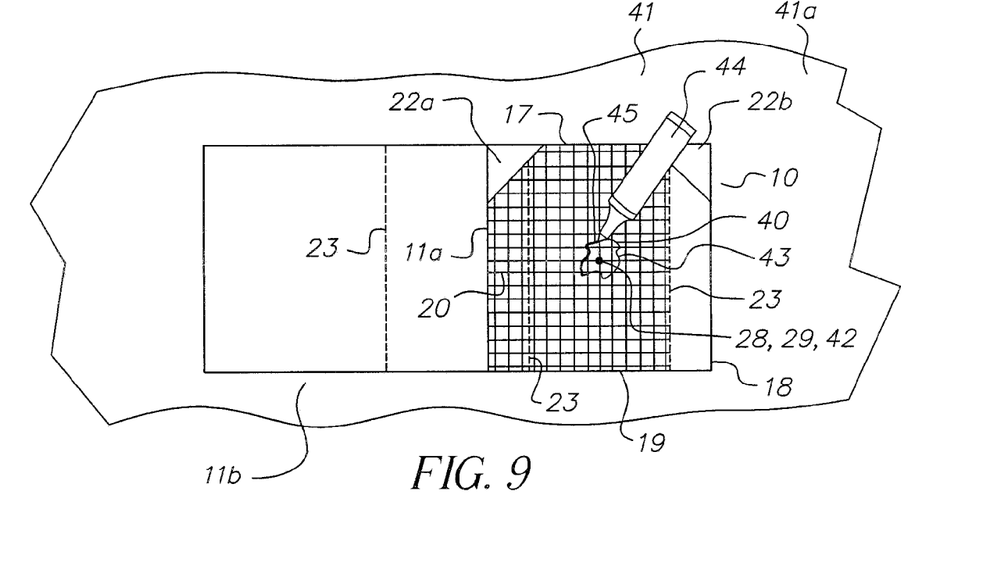
Figure 10:
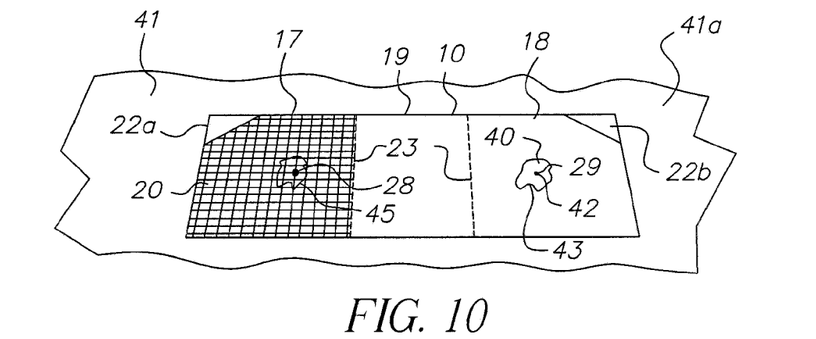

Using tab 22a, a corner of top layer 11a of guide sheet 10 is manually peeled upwards away from middle layer 11b lifting the first portion 17 and intermediate portion 19, so that first portion 17 is folded along fold lines 23 (FIG. 7) creating a tri-fold or accordion fold over second portion 18 (FIG. 8). The first portion 17 now overlays to partially cover second portion 18, the outline 43 drawn thereupon, and lesion 40, thereby placing guide sheet 10 in a folded state (FIG. 9). The intermediate portion 19 being sandwiched between portions 17 and 18 in such folded state as shown. With the first portion 17 folded flat over the second portion 18 of the guide sheet 10, fiducial mark 28 of grid 20 aligns with fiducial mark 29 along the second portion 18. The outline 43 of lesion 40 is then retraced with ink from pen 44 to produce a matching outline 45 onto the first portion 17 along grid 20, as shown in FIG. 9. Although outline 45 is described herein when guide sheet 10 is in its folded state, any marks may be located with pen 44 along grid 20 at one or more location as desired in relation to any areas of interest viewable on tissue 41, which may or may not represent a lesion. The first portion 17 is unfolded back to its original position on layer 11b to return guide sheet 10 to its original unfolded state (FIG. 10). After such planimetry to provide outline 45 on the guide sheet 10 is completed, all the layers 11a, 11b, and 11c of the intermediate and second portions 19 and 18 are removed from tissue 41, leaving first portion 17 affixed to tissue 41. This is achieved by manually holding first portion 17 in place, and then manually tearing along the perforations of fold line 23 closest to first portion 17 through layers 11a, 11b, and 11c, thereby leaving a cut edge 46. The first portion 17 with grid 20 and outline 45 (and/or any other marked locations) can now serve as guide member 12 for mapping during examination of exposed lesion 40 on tissue 41 (FIG. 11), and thus first portion 17 will be referred to as guide member 12 hereinafter.

Figure 12A:
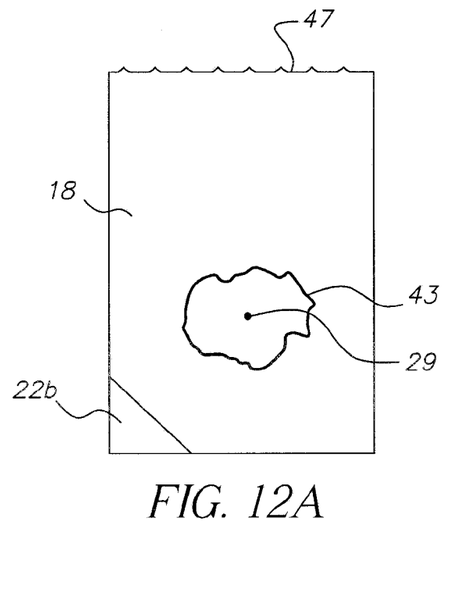
Figure 12B:
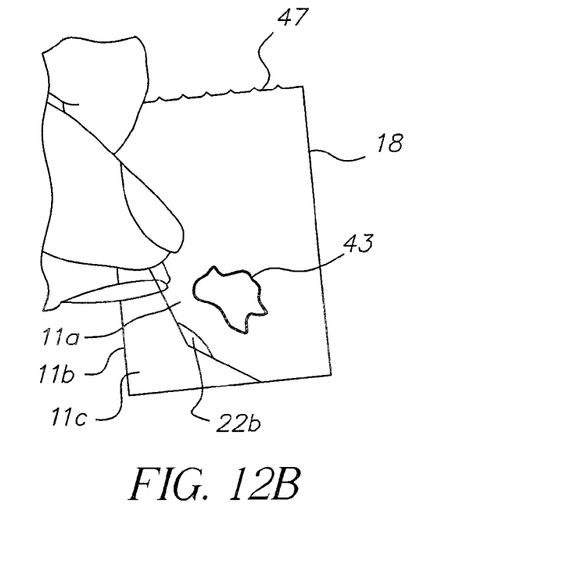

The second portion 18 with outline 43 of lesion may be removed from intermediate portion 19 by tearing along perforations of fold line 23 closest to second portion 18 to provide cut edge 47 (FIG. 12A). The intermediate portion 19 is then discarded. The layer 11a providing second portion 18 is then peeled away using tab 22b from layers 11b and layer 11c (FIG. 12B). The removed layers 11b and 11c are discarded, and the second portion 18 with outline 43 retained as a baseline record if desired.

Figure 13A:
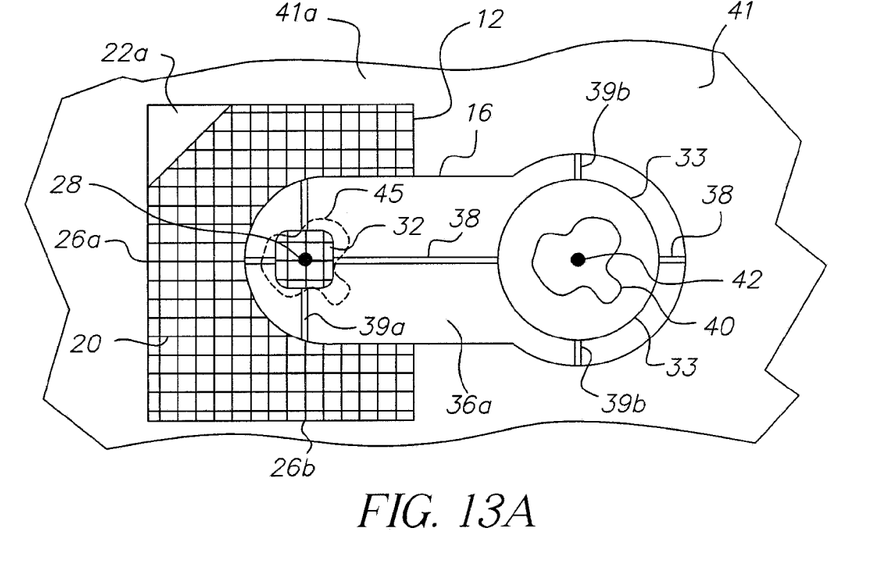
FIG. 13A shows an example of the template device over the guide member of FIG. 11 illustrating the spatial correlation of the grid and lesion outline on the guide member with the actual lesion in the tissue viewed in the second and first apertures, respectively, of the template device.
Figure 13B:
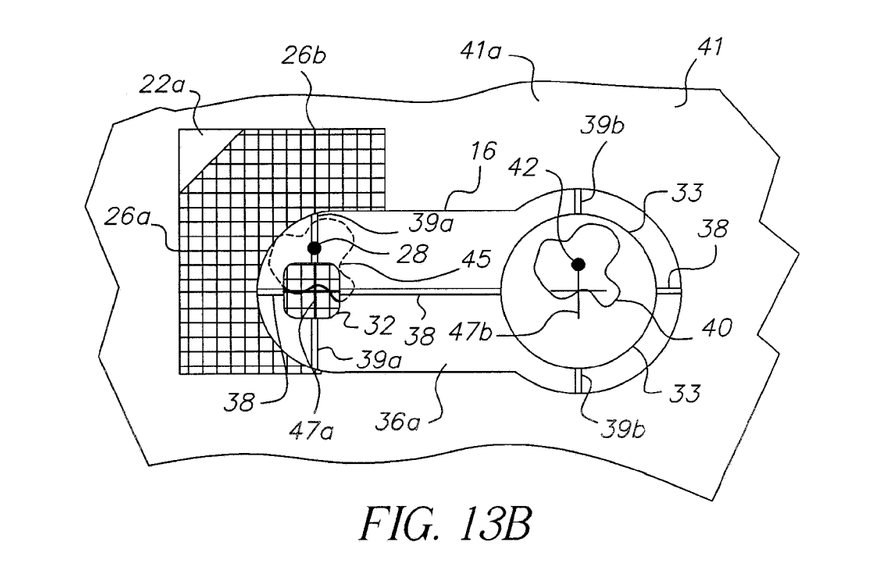
FIG. 13B shows another example similar to FIG. 13A of the template device over the guide member of FIG. 11 in which the template device has been moved along the guide member while maintaining the spatial correlation between the actual lesion and the lesion outlined on the guide member.
Figure 13C:
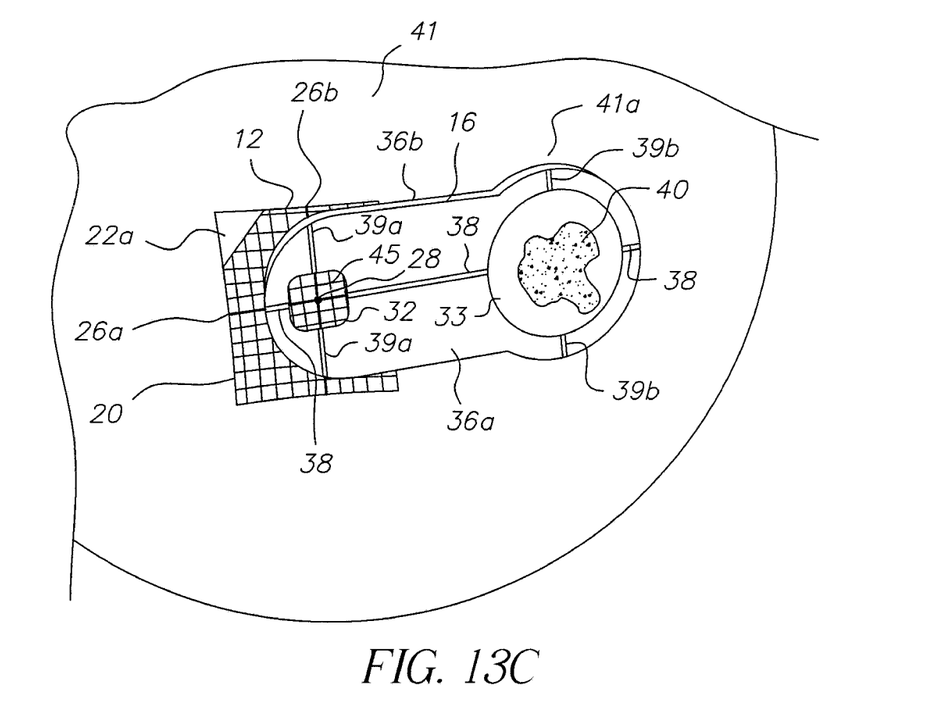
FIG. 13C is a perspective view of an example of the template device of FIGS. 3A, 3B, and 3C when positioned with respect to guide member of FIG. 11 prior to imaging with the microscope to illustrate template device being flexible so as to follow the curved skin tissue, such as the forehead depicted.

Referring to FIG. 13A, template device 16 is shown applied to surface 41a of tissue 41 prior to start of imaging so that lesion 40 is viewable through aperture 33 of the template device with the dot 42 on the lesion centered between horizontal lines 38 and vertical lines 39b on the template device, and grid 20 of the guide member 12 is viewable through aperture 32 with fiducial mark 28 on the grid aligned with (or centered between) horizontal lines 38 and vertical lines 39a of the template device. Such fiducial mark 28, axes 26a, 26b, and/or grid lines parallel to such axes provide features on the surface of the guide member 12 for aligning template device 16 with respect the guide member 12 viewable through aperture 32, thereby enabling spatial correlation to tissue 41 with lesion 40 adjacent the guide member as established using guide sheet 10 as described above. This being the case since guide member 12 was positioned upon tissue 41 so that the point provided by fiducial mark 28 upon the guide member 12 and dot 42 upon the lesion 40 are in a same spatial relationship to each other as the first and second apertures are to each other along template device 16 at their respective centers. Thus, horizontal lines 38 on either side of aperture 32 align along x axis 26a of grid 20, and vertical lines 39a on either side of aperture 32 align along y axis 26b of grid 20. Lines 38 and 39a in this manner provide cross-hairs for selecting target locations on grid 20 which spatially correlate to locations along the lesion 40 centered with cross-hairs provides by lines 38 and 39b on either sides of aperture 33. As shown in FIG. 13B, this spatial correlation is maintained so long as lines 38 are aligned parallel with other x lines along grid 20 parallel with x axis 26a, and lines 39a are aligned parallel to other y lines along grid 20 parallel to y axis 26b. For purposes of illustration, crosses 47a and 47b are drawn in apertures 32 and 33, respectively, are provided to illustrate in FIG. 13B location targeting in such apertures when template device 16 is moved with respect to tissue 41 and guide member 12 to another different location than center along grid 20. In particular, the location selected in FIG. 13B along outline 45 spatially corresponds to one edge of lesion 40 where the margin between healthy and unhealthy tissue may exist along the tissue surface 41a. An example of template device 16 is also shown in FIG. 13C positioned with respect to guide member 12 and a lesion 40 prior to imaging being carried out. Unlike FIG. 1, FIG. 13C shows an example where guide member 12 has four, rather than eight labelled axes.

Figure 14:
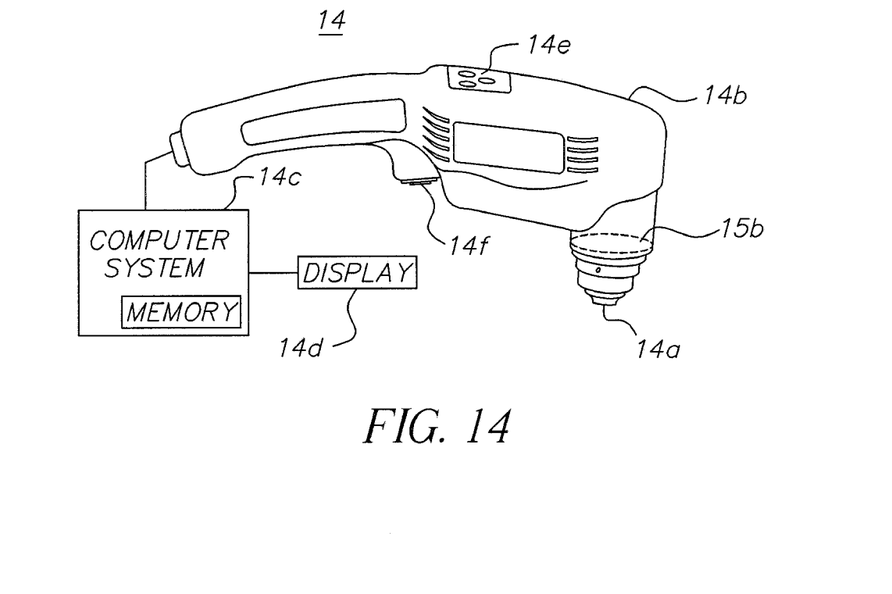
FIG. 14 is a block diagram of a confocal imaging system with a handheld confocal probe as provided by a VivaScope® confocal microscope.

Referring to FIG. 15, with template device 16 properly aligned along guide member 12, the front nose end 14a of probe 14b of microscope 14 of FIG. 14 is placed in aperture 33 so that a plate or window 15a at the end of the nose 14a lies against the tissue to present to the microscope tissue restricted by such aperture, as shown in FIG. 15. Preferably, a few drops of mineral oil are placed onto lesion 40 and tissue surface 41a in aperture 33 prior to placement of front nose 14a into aperture 33. Such mineral oil or other liquid medium enhances optical coupling and index matching between the tissue 41 and window 15a and hence optics of the microscope 14, which includes at least objective lens 15b (schematically illustrated as being present in probe 14a, where its position is not to scale).

The microscope 14 is prepared for imaging and operated in a typical manner for capturing confocal images as specified by the manufacture of the microscope. Such microscope 14 typically has a computer system 14c which is operated to show on display 14d captured microscopic sectional images of tissue 41 and storing them in memory of computer system 14c. In the case where microscope 14 is provided by a confocal microscope, VivaScope® 3000, manufactured by Caliber I.D., of Henrietta N.Y., laser illumination is scanned below the surface 41a of the tissue 41 using objective lens 15b for focusing the illumination (see for example light rays 15c) into tissue 41, and returned illumination is optically formed into microscopic sectional images (confocal images) by computer system 14c for viewing on display 14d and storage in memory of computer system 14c. Confocal images are thus acquired by microscope 14 to enable examination at selected locations in tissue mapped with respect to the tissue surface along grid 20 in aperture 32 as template device 16 is moved in alignment with the grid's x and y axes at each such selected location. Such locations selected may be the same or different than those marked on guide member 12. While microscope 14 is preferably a handheld confocal microscope as shown in FIG. 14, other microscopes may be used which can also optically form microscopic sectional images under the surface of the tissue, such as those which operate by two-photon microscopy or optical coherence tomography or interferometry (OCT).

In the preferred embodiment, prior to start of imaging using microscope 14 a record (or worklist) is first established in memory of the computer system 14c for the imaging session with information about the patient, such as name, birth date, sex, and site on the patient where the lesion 40 is located, such as left or right cheek or forehead. During the session, captured images are stored in memory of computer system 14c linked to such record. With template device 16 aligned along tissue 41 and guide member 12, as described earlier in connection with FIG. 13A (i.e., grid 20 lines are aligned with lines 38 and 39a on template device 16 with aperture 32 centered over fiducial mark 28), template device 16 is at (0,0) location along the x,y grid 20 which spatially corresponds with (0,0) location at dot 42 along lesion 40 in aperture 33. The probe 14b is maintained in the aperture 33 of template device 16 as different locations for capturing images are mapped using a (x,y) Cartesian coordinate system along grid 20, where origin (0,0) is denoted by position of mark 28 where x and y axes 26a and 26b, respectively, intersect.

For example, microscope 14 is first operated to capture one or images at the (0,0) location. Such images preferably are captured in a stack at different depth levels under the tissue surface 41a centered at dot 42 of the lesion 40. A user interface (e.g., keyboard, touchscreen, or mouse) of computer system 14c may be used by an operator to actuate capture of such stack of images, or buttons 14e or trigger 14f may be used to signal computer system 14c to effect such capture, as desired. The images captured are stored in memory of computer system 14c and shown in display 14d to verify that they contain images of the epidermis, superficial dermis, and the lesion, such as a BCC (Basal Cell Carcinoma) tumor. If the stack of images are not of acceptable quality on display 14d, the images are deleted from memory of the computer system 14c and re-captured before moving the template device 16 to a next location along grid 20 while maintaining spatial alignment between template device 16 and grid 20 as described earlier in connection with FIGS. 13A and 13B. Stacks of images may be similarly be captured by template device 16 being moved along grid 20 to guide system 11 to each location as desired. Preferably, locations are selected at regular intervals along each of the eight axes or four axes as numbered along grid 20 of FIG. 1. Thus after imaging at the (0,0) location is completed, the next location along grid 20 is selected along axis number one in FIG. 1, such as (0,1.5) grid location, and a second stack of images are captured by microscope 14. Additional stacks are similarly captured (0, 3.0), (0,4.5), etc. at each grid location along axis number one until the end of the grid 20 is reached. Each series of stack images captured are stored in the order of capture along a common axis are associated with the same identifier, such as A1, for association in the record linked to captured images. Optionally, each stack of images may have a different identifier, as desired. After each captured stack, the operator should verify that it contains sufficient images of the epidermis, superficial dermis, and the BCC tumor for later analysis before moving to the next location along that axis. After images are captured along the axis number one, microscope 14 images are similarly captured along each of the axes as desired and denoted A2, A3, and A4, and if desired A5, A6, A7, and A8. Each series of images along each axis of the 1-4 or 1-8 axes may start at (0,0) or at the next interval outward along such axis. In this manner such numbered axes add a directional component to the x,y coordinate system on guide member 12. Other manner of selection of locations along grid 20 may be used than described above, and optionally single confocal image(s) at desired depths from the surface may be captured rather than a stack. In this manner, microscope 14 may be operated to capture one or more images of the tissue via second aperture 33 at one or more locations in tissue 41 each spatially correlated with a location selected or being mapped along guide member 12 in the first aperture 32 with respect to lesion 40. For purposes of illustration, FIGS. 13A and 13B may represent an example of the positioning of guide member 12 and the template device 16 when the microscope 14 is positioned for imaging via aperture 33 at two different locations along the lesion 40 which are spatially correlated to two different locations along the guide member 12, i.e., one centered along axes 26a and 26b (FIG. 13A), and the other denoted by cross 47a (FIG. 13B).

Optionally, instead or additional, one or more locations may be selected in accordance with information recorded on grid 20 with pen 44 when located over the lesion (see FIG. 9) such as along outline 45 or other marks recorded on grid 20 of areas of interest on tissue 41 within, along, or outside lesion 40. Further, during imaging a mark may be made on grid 20 via aperture 32, such as using a pen 44, at a position centered between lines 38 and 39a as cross-hairs indicating where one or more confocal images were acquired of a particular location of interest with respect to lesion 40 as may be recorded on grid 20. One or more such marks may be applied each associated with a different location along grid 20 and thus a different location along lesion 40. Each mark so applied onto grid may include identification information to reference the mark with such acquired images, such information may be a number, arrow, color, code, or identifier, for use in association with captured images which may optionally be stored in association with such one or more images in memory of the computer system, as desired.

After the imaging session is completed, probe 14b is removed from template device 16, and the template device 16 is lifted from tissue 41. The guide member 12 is removed from tissue 41 by peeling away all of its layers 11a, 11b, 11c, and top layer 11a with grid 20 is then peeled away using tab 22a from layers 11b and layer 11c. The removed layers 11b and 11c are discarded, and the guide member 12 retained as a record, and for future use such as described below.

In this manner, the guide member maps the locations of confocal images captured in skin tissue 41 having a lesion 40 creating a physical record with respect to a grid 20 and/or axes 25, 26a, 26b along the guide member. The mapped locations along the grid and/or axes can then be used for directing treatment were unhealthy or abnormal tissue as determined in such captured images, thereby minimizing risk of harm to healthy tissue which may lie near the lesion.

Figure 16A:
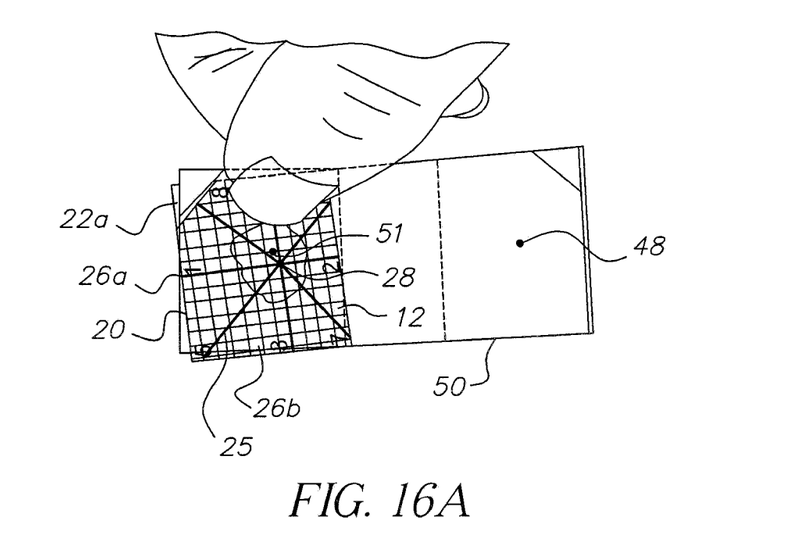
FIG. 16A is a top view of another guide sheet which is the same as tracing guide sheet of FIG. 1 without the grid in which manual application of the guide member 12 onto such another guide sheet is shown for use in future imaging by the microscope of the system, where the guide member of FIG. 11 is shown removed from the tissue and is in the process of manually placement to such another guide sheet.
Figure 16B:
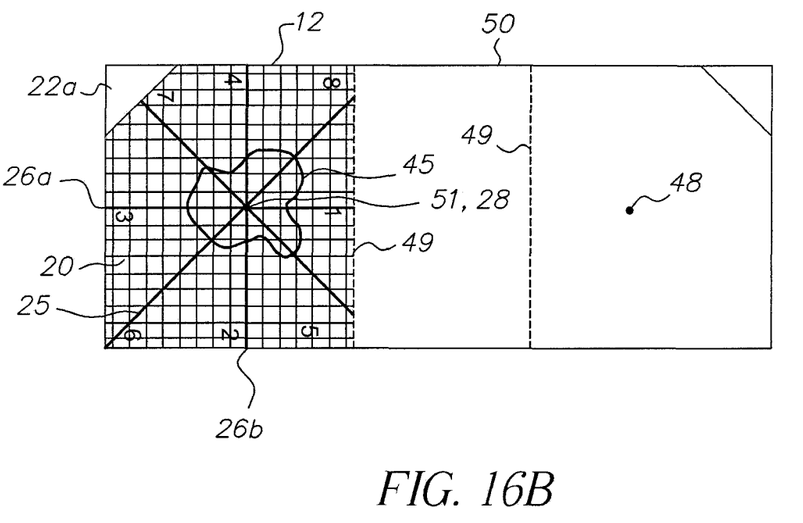
FIG. 16B is a top view of the same guide sheet of FIG. 16A with the guide member of FIG. 11 positioned in the same orientation as in the guide sheet of FIG. 10 so that the guide member can be affixed back to the tissue and be used to image using the template device of FIGS. 3A, 3B, and 3C, and microscope of FIG. 14 in the system at the same or different locations as previously imaged.

Preferably, guide member 12 is applied to the top layer of a blank sheet 50 as shown in FIG. 16A, which is identical to guide sheet 10 but without grid 20, and having fiducial marks 51 and 48 spatially positioned along sheet 50 identical to fiducial marks 28 and 29, respectively, along guide sheet 10. The guide member 12 adheres by static cling to blank sheet 50. The guide sheet 12 is aligned along blank sheet 50 so that its fiducial mark 28 at (0,0) aligns with fiducial mark 51, and grid 20 aligns square with the edges of sheet 50 as shown in FIG. 16B. Blank sheet 50 thereby becomes a new guide sheet 10 similar to FIG. 10 (but without outline 43 of the lesion) for placement back on the tissue surface 41a at a future time, such as 12 weeks, for reimaging by microscope 14 at the same or different location(s) as before to assess for any changes in status of the tissue and lesion 40 therein.

Figure 11:
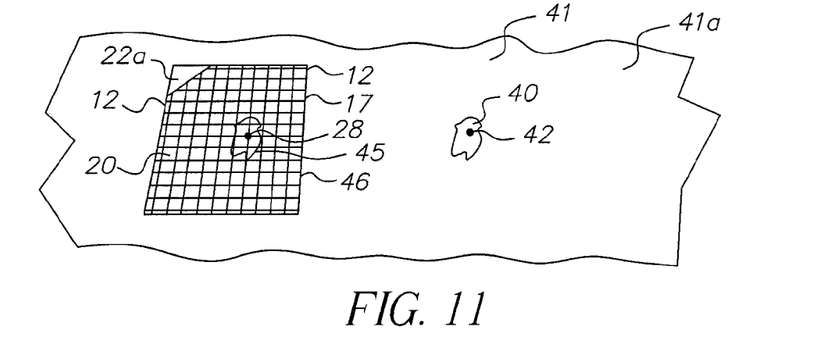

Optionally, sheet 50 when applied by adhesive material to tissue 41 may be similarly folded over along fold lines 49 in the same manner as FIGS. 8 and 9 to verify that outline 45 aligns to (or matches with) outer edges of the lesion 40 as before (as close as possible if not exactly) when fiducial mark 48 is aligned over dot 42 that was previously applied to the lesion. When folded back into an unfold state, guide member 12 is once again ready for use in system 11 with template device 16 and microscope 14 as described earlier after removal of rest of the sheet 50 along perforations of fold line 49 closest to the guide sheet so that guide member 12 again is located as shown in FIG. 11 with respect to lesion 40. To assist is precisely locating sheet 50 onto tissue 41 to match that of guide sheet 10, digital photographs may have been taken when guide sheet 10 when originally placed onto tissue 41.

In this manner, guide member 12 after removal from the skin tissue 40 can be placed back onto the same tissue at a future time in the same orientation thereby enabling recapture of newer images by the confocal microscope 14 of system 11 at the same locations with respect to the surface as previously captured. This facilitates examination of any microscopic changes (healthy to unhealthy tissue, or vice versa) in the tissue imaged which may have taken place between such different times of capture, such as after applied non-invasive treatment (such as ingested or topical drug therapy, or optical therapy), or non-treatment observation.

Additionally, the tracing guide sheet 10 may be elongated from that shown in the figures and described above, so that first, second, and intermediate portions 17, 18 and 19 are square and of equal dimension. For example, the length of the guide sheet may be 3 inches long with each portion 17, 18, and 19 square with 1 inch per side. Thus, when in a folded state as shown in FIGS. 8 and 9, top layer 11a covers exactly second portion 18, as well as intermediate portion 18, sandwiched there between, rather than substantially covering portion 18. Fiducial marks 28 and 29 are then centered along their respective first and second portions, and grid 20 extends equally along x and y axes. Template device 16 is also elongated so that the distance between the centers of apertures 32 and 33 equals the distance, such as 2 inches, between marks 28 and 29. Further sheet 46 is similarly elongated to match dimensions of an elongated sheet 10.

From the foregoing description, it will be apparent that an improved system and method for mapping the locations of captured confocal images of a lesion in skin tissue has been provided. Variations and modifications in the herein described system, method, guide member and template device in accordance with the invention will undoubtedly suggest themselves to those skilled in the art. Accordingly, the foregoing description should be taken as illustrative and not in a limiting sense.

The invention claimed is:

1. A system for mapping locations of captured images of a lesion in tissue comprising:
a guide member having a surface;
a template device having a first aperture located over said surface of said guide member, and a second aperture located over said tissue having at least said lesion;
said guide member being positioned upon the tissue so that a certain point or mark upon said surface of said guide member and a point or dot upon a lesion in the tissue are in a same spatial relationship to each other as said first aperture and said second aperture are to each other along said template device at their respective centers;

a microscope operated to capture one or more images of the tissue, via said second aperture, at one or more locations in said tissue, in which each of said one or more locations when centered in said second aperture spatially corresponds with a location selected or being mapped along said guide member when centered in said first aperture with respect to said lesion;

wherein said template device is movable to at least two different ones of said location along said guide member each spatially corresponding to a different one of said one or more locations in said tissue where said one or more images are captured by said microscope; and wherein prior to imaging and placement of said template device upon said tissue, said guide member represents a first section of a guide sheet upon the tissue having said first section and a second section, said first and second sections each having one of a pair of first marks at a distance equal to the distance between centers of said first and second apertures of said template device, a first of said pair of first marks upon the first section represents said certain point or mark upon the surface of said guide member, a second of said pair of first marks upon the second section is aligned over said point or dot upon said lesion in the tissue, and said second section being then removed from said first section for use of said first section as said guide member.

2. The system according to claim 1 further comprising lines along said guide member defining a coordinate system oriented with respect to said certain point or mark of said guide member to assist in selection or mapping said location along said guide member representing where each of said one or more locations in said tissue said one or more images are captured by said microscope.

3. The system according to claim 2 wherein said lines defining said coordinate system form at least part of a grid on said surface of said guide member, and said grid comprises at least x and y orthogonal axes extending through a center origin of said coordinate system that defines said certain point or mark upon the surface of said guide member.

4. The system according to claim 3 wherein said lines defining said coordinate system further comprise diagonal axes through said center origin of said coordinate system.

5. The system according to claim 3 wherein said center origin of said coordinate system spatially correlates with said point or dot upon a lesion which represents a center of said lesion.

6. The system according to claim 3 wherein said template device has a first dimension extending longitudinally along said template device centrally through said first aperture and said second aperture, said first dimension being aligned parallel to said x axis of said grid, and said first aperture and said second aperture each have a centrally oriented second dimension orthogonal to said first dimension aligned parallel to said y axis of said grid.

7. The system according to claim 6 wherein said template device has a surface with features denoting said first and second dimensions for aligning said template device with respect to said grid.

8. The system according to claim 1 wherein, prior to removal of said second section from said first section, said second section of said guide sheet is located upon the tissue with said lesion, and said first section is folded over said second section aligning said pair of first marks with each other to place said guide sheet in a folded state, and in said folded state one or more second marks related to said lesion under said first and second sections are applied to said first section, so that when said first section is folded back to place said guide sheet in an unfolded state and said second section is removed from said first section, said first section is utilized as said guide member with said one or more second marks spatially correlated with said lesion.

9. The system according to claim 8 wherein said one or more second marks represents at least an outline tracing a boundary of the lesion.

10. The system according to claim 1 wherein said surface of said guide member has one or more marks applied to said guide member related to said lesion different from said certain point or mark upon the guide member, and said one or more marks being used in positioning said template device when moved to one or more of said at least two different ones of said location along said guide member.

11. The system according to claim 1 wherein said microscope is a confocal microscope and said one or more images are one or more microscope sectional images captured below surface of said tissue.

12. The system according to claim 1 wherein said guide member represents an upper surface of a sheet having one of more layers which are affixed temporarily to said tissue.

13. The system according to claim 1 wherein said template device is flexible to adapt to curvature along the tissue.

14. The system according to claim 1 wherein said microscope has a front end received in said second aperture of said template device.

15. A method for mapping locations of captured images of a lesion in tissue comprising steps of:

placing a first section of a guide sheet upon the tissue having a first section and a second section, in which said first and second sections each have one of a pair of first marks at a distance equal to the distance between centers of first and second apertures of a template device, in which a first of said pair of first marks upon the first section represents a certain point or mark, a second of said pair of first marks upon the second section is aligned over a point or dot upon said lesion in the tissue;

removing said second section from said first section, wherein said first section represents a guide member having a surface;

positioning a template device having a first aperture located over said surface of said guide member, and a second aperture located over said tissue having at least said lesion, in which said certain point or mark upon the first section and said point or dot upon a lesion in the tissue are in a same spatial relationship to each other as the first aperture and the second aperture are to each other along the template device at their respective centers;

capturing one or more images of the tissue using a microscope via said second aperture at one or more locations in said tissue, in which each of said one or more locations when centered in said second aperture spatially corresponds with a location selected or being mapped along said guide member when centered in said first aperture with respect to said lesion; and moving said template device to at least two different ones of said location along said guide member each spatially corresponding to a different one of said one or more locations in said tissue where said one or more images are captured by said microscope.

16. The method according to claim 15 further comprising step of providing lines along the guide member defining a coordinate system oriented with respect to said certain point or mark of said guide member, wherein said lines defining said coordinate system form at least a grid to assist in selection or mapping said location along said guide member representing where each of said one or more locations in said tissue said one or more images are captured by said microscope.

17. The method according to claim 15 further comprising step of affixing said guide member to said tissue prior to said moving step being carried out.

18. The method according to claim 16 wherein said step of positioning said template device and said step of moving said template device each utilize features on said template device in alignment with at least part of said grid of said guide member.

19. The method according to claim 15 further comprising steps of:
removing said template device and said guide member from said tissue after said capturing step is carried out;
realigning said guide member in same said spatial relationship to said tissue with said lesion after said removing step is carried out;
relocating said template device upon said tissue to position said first aperture over said guide member and said second aperture located over said tissue after said realigning step is carried out; and
capturing additional one or more images via said second aperture of said template device at different or same said one or more locations in said tissue after said relocating step is carried out.

20. The system according to claim 3 wherein said template device is aligned with at least part of said grid of said guide member.

21. The system according to claim 1 wherein said template device is moveable over said tissue and said guide member when said guide member is affixed upon the tissue.

22. The system according to claim 1 wherein said first aperture and said second aperture are at different ends of said template device.

23. The system according to claim 1 wherein after said one or more images are captured by said microscope said template device and said guide member are removed from said tissue, and said guide member at a future time being realigned in same said spatial relationship to said tissue with said template device being relocated upon said tissue having said first aperture located over said guide member and said second aperture located over said tissue so that said microscope captures additional one or more images via said second aperture of said template device at different or same said one or more locations in said tissue.

24. The system according to claim 10 wherein said one or more marks are manually applied to said guide member prior to imaging of said tissue by said microscope.

25. The system according to claim 24 wherein said one or more marks represent an outline of said lesion adjacent said guide member.

26. The system according to claim 10 wherein at least one of said one or more marks is manually applied via said first aperture to said guide member to denote a site along the tissue during imaging of said tissue by said microscope via said second aperture of said template device.

27. A system for mapping locations of captured images of a lesion in tissue comprising:
a guide member having a surface with at least a grid;
a template device having a first opening and a second opening, in which said first opening is located over said surface of a guide member, and said second opening is located over said tissue, in which said guide member is positioned upon the tissue so that a certain point or mark on said grid and a point or dot upon a lesion in the tissue are in a same spatial relationship to each other as the first aperture and the second aperture are to each other along the template device at their respective centers;
a microscope operated to capture one or more images of the tissue, via said second opening, at one or more locations along said tissue having a lesion, in which each of said one or more locations when centered in said second opening spatially corresponds with a location upon said guide member when centered in said first opening, wherein said template device is movable along said guide member and said tissue to select different ones of said one or more locations along said tissue while maintaining alignment of features along said template device to at least part of said grid of said guide member; and
wherein prior to imaging and placement of said template device upon said tissue, said guide member represents a first section of a guide sheet upon the tissue having said first section and a second section, said first and second sections each having one of a pair of first marks at a distance equal to the distance between centers of said first and second openings of said template device, a first of said pair of first marks upon the first section represents said certain point or mark upon the guide member, a second of said pair of first marks upon the second section is aligned over said point or dot upon said lesion in the tissue, and said second section being then removed from said first section for use of said first section as said guide member.

28. The system according to claim 27 wherein said guide member is affixed to said tissue when said template device is moved along said guide member and said tissue.

29. The system according to claim 27 wherein said first opening and said second opening are at different ends of said template device.

30. The system according to claim 1 further comprising lines forming a grid along said surface of said guide member which defines a coordinate system oriented with respect to said certain point or mark upon said guide member.

31. The system according to claim 1 wherein said point or dot upon said lesion is at a user defined position with respect to said lesion.

32. The method according to claim 15 further comprising the step of providing one or more marks upon said guide member related to said lesion different from said certain point or mark upon the guide member, wherein said moving step utilizes said one or more marks in positioning said template device to one or more of said at least two different ones of said location along said guide member.

* * * * *